United States Patent
Cesarczyk et al.

[11] Patent Number: 6,150,178
[45] Date of Patent: Nov. 21, 2000

[54] DIAGNOSTIC TESTING DEVICE

[75] Inventors: Edward J. Cesarczyk, North Easton; Peter P. Phildius, Wayland, both of Mass.

[73] Assignee: Avitar, Inc., Canton, Mass.

[21] Appl. No.: 09/275,476

[22] Filed: Mar. 24, 1999

[51] Int. Cl.[7] .................................................. G01N 33/48
[52] U.S. Cl. ........................ 436/165; 436/169; 422/58; 422/61; 422/100
[58] Field of Search .................. 422/58, 61, 100, 422/101; 436/165, 169, 177–178

[56] References Cited

U.S. PATENT DOCUMENTS

| | | | |
|---|---|---|---|
| 5,000,193 | 3/1991 | Heelis et al. | 128/760 |
| 5,022,409 | 6/1991 | Goldstein et al. | 128/760 |
| 5,260,031 | 11/1993 | Seymour | 422/101 |
| 5,268,148 | 12/1993 | Seymour | 422/101 |
| 5,283,038 | 2/1994 | Seymour | 422/101 |
| 5,339,829 | 8/1994 | Thieme et al. | 128/760 |
| 5,376,337 | 12/1994 | Seymour | 422/101 |
| 5,380,492 | 1/1995 | Seymour | 422/58 |
| 5,393,496 | 2/1995 | Seymour | 422/101 |
| 5,479,937 | 1/1996 | Thieme et al. | 128/760 |
| 5,494,646 | 2/1996 | Seymour | 422/101 |

*Primary Examiner*—Lyle A. Alexander
*Attorney, Agent, or Firm*—George W. Neuner; Dike, Bronstein, Roberts & Cushman, LLP

[57] ABSTRACT

A specimen collecting and testing device has a housing containing a test membrane. An elongated handle having a foam member is slidably received in the housing. Once the foam member obtains a specimen, the housing is moved with respect to the handle and the foam member is moved inside the housing and slid past the test membrane. In so doing, specimen is delivered to the test membrane. The test membrane may then be observed for optical changes in the case of an instant-type test, or removed for further processing. The device is particularly useful for collecting samples of urine or oral fluid for use in drug testing, pregnancy testing and the like; for testing of specimen for any of a variety of analytes such as HIV, hepatitis B, hepatitis C, etc.; and, for collecting samples of DNA for PCR testing.

34 Claims, 8 Drawing Sheets

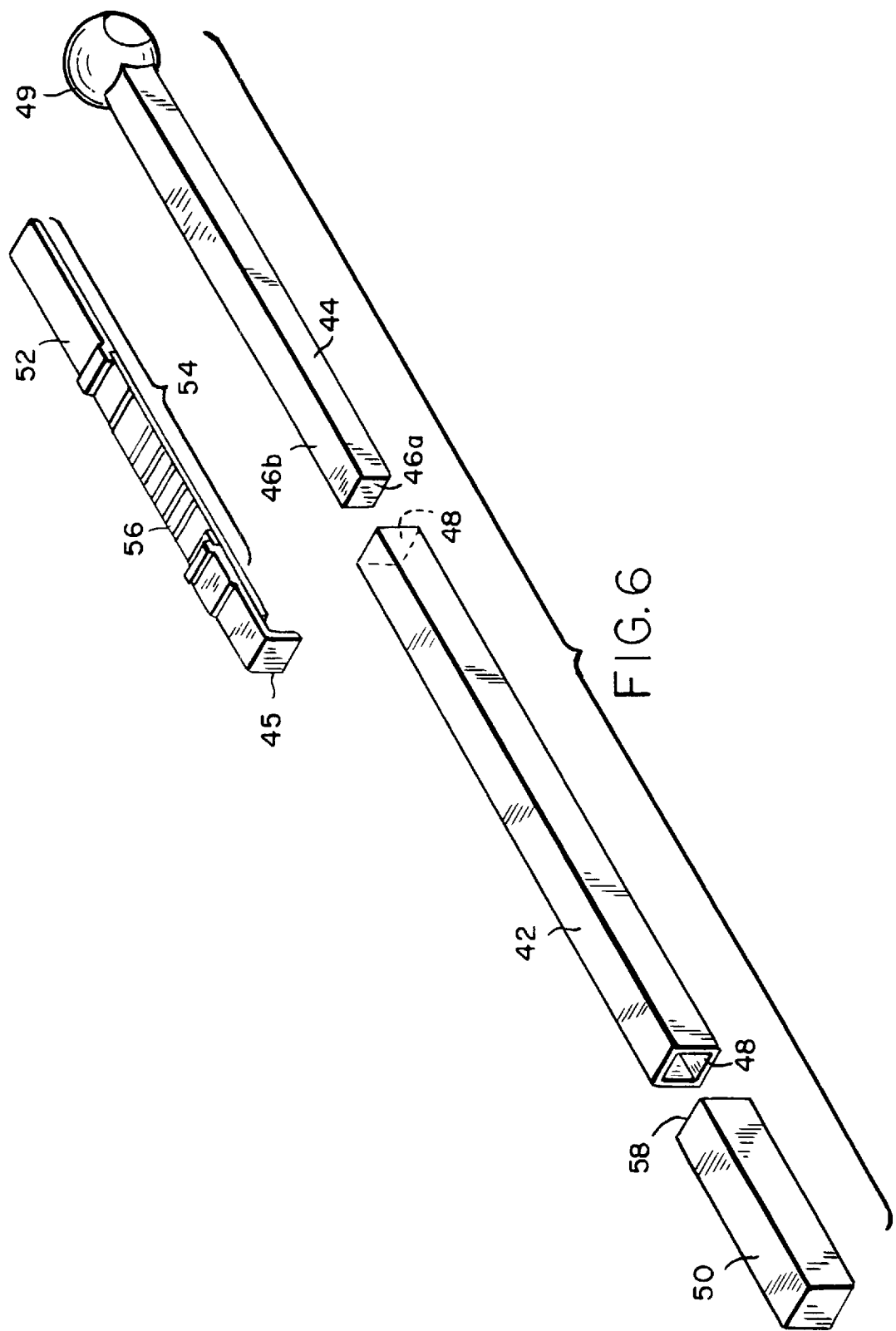

DIAGNOSTIC TESTING DEVICE

FIELD OF THE INVENTION

The present invention is related to devices for the collection of specimen, e.g., oral fluid, urine, or the like, and their diagnostic testing. The device of the present invention provides an absorbent foam member on a handle, and a housing for delivering the fluid specimen from the foam member onto a test membrane, and is particularly useful for the collection and testing of a specimen from a mammal while maintaining aseptic conditions.

BACKGROUND OF THE INVENTION

Various methods and devices have been used to collect and deliver specimen for diagnostic testing. One conventional method for collecting an oral fluid specimen is to use a cotton swab. The oral fluid sample can then be applied to a test device by contact with the swab or the sample can be rinsed from the swab.

Various devices comprising test tube like structures with sample absorbing means have been described for collecting biological samples for diagnostic testing. Examples of such devices are described in U.S. Pat. Nos. 4,123,224, 5,000,193, 5,022,409, 5,260,031, 5,268,148, 5,283,038, 5,339,829, 5,376,337, 5,380,492, 5,393,496, 5,479,937 and 5,494,646.

In a copending application, U.S. Ser. No. 08/712,682, a simple device for collecting and delivering a specimen for diagnostic testing is described. In accordance with the disclosure, a specimen collecting device comprises an elongated foam member having a longitudinal axis and an uncompressed cross sectional area, the elongated foam member being circumscribed by a hollow tubular member along a portion of the longitudinal axis, the hollow tubular member having a cross sectional area less than the uncompressed cross sectional area of the foam member so that the foam member is compressed along the circumscribed portion.

In another copending application, U.S. Ser. No. 08/869,105, an improved device for collecting and delivering a specimen for diagnostic testing is disclosed, wherein the device provides a simple and convenient method for extracting the sample from a foam member. According to the disclosure, an embodiment of a specimen collecting device includes an elongated foam member having a longitudinal axis and an uncompressed cross sectional area, the elongated foam member being circumscribed by a hollow tubular member along a portion of the longitudinal axis, the hollow tubular member having a cross sectional area less than the uncompressed cross sectional area of the foam member so that the foam member is compressed along the circumscribed portion. Around the hollow tubular member is a flexible sleeve member having a first end that fits snugly around the hollow tubular member and a second end with an enlarged diameter that can surround the uncompressed foam member. Conveniently, the sleeve member can be moved along the hollow tubular member to cover and uncover the portion of the foam member that is not circumscribed by the hollow tubular member. Further, by sliding the flexible sleeve member along the hollow tubular member to cover the foam member and by squeezing the foam member through the flexible sleeve member, a portion of the fluid absorbed by the foam may be extracted.

SUMMARY OF THE INVENTION

The present invention provides a simplified and improved device for the collecting and diagnostic testing of a specimen, wherein the device provides a simple and convenient method for obtaining a specimen sample on a foam member and testing with a diagnostic test strip. The device provides an integral test membrane, onto which the collected sample is delivered.

In accordance with the present invention, a specimen collecting and testing device comprises an elongated handle member having a foam member at an end thereof. The handle member passes through a hollow, elongated housing member, which holds the test membrane in a stationary position for contact with the foam member. The foam member is positioned outside the housing member for sample gathering. When the handle member is withdrawn, the foam member is drawn into the housing member and across the surface of the test membrane, thereby delivering the sample to the test membrane.

According to one feature, the foam member comprises a material which, when wetted by the sample, will expand from its dry configuration. When wetted, the foam member will have a cross sectional area that is greater than that of the housing member such that, when the handle member is withdrawn so as to draw the wetted foam member into the housing member, the foam member is compressed as it is drawn across the surface of the test membrane. The compression of the foam member and/or capillary movement of the liquid will express specimen onto the test membrane to react with the test chemistry carried thereby.

A preferred embodiment of the invention utilizes a hydrophilic microporous material for the test membrane, whereby capillary action carries the liquid into the test membrane. Thus, the hydrostatic forces resulting from compression of the foam member are not relied upon for the operability of the device.

In one embodiment, the foam member has a longitudinal axis and an uncompressed cross sectional area. The elongated foam member is circumscribed by a hollow, elongated housing along a portion of the longitudinal axis. The hollow, elongated housing has an interior cross sectional area that is less than the uncompressed cross sectional area of the foam member so that the foam member is compressed along the circumscribed portion to deliver the sample to the test membrane held inside the hollow, elongated housing.

The diagnostic testing device of the present invention is particularly useful for collecting a sample of a fluid specimen and delivering the sample to a test membrane for a rapid one-step drug abuse test. It can also be used to provide fluid samples, particularly oral fluid or urine samples, for DNA testing for forensic and paternal identification, RNA testing, antibody testing, testing for particular drugs, and other similar diagnostic procedures. The testing device of the present invention provides a simple and inexpensive method for collecting and testing the oral fluid sample. Further, in preferred embodiments of the invention, the foam member of the diagnostic testing device will provide more consistent and accurate samples.

BRIEF DESCRIPTION OF THE DRAWINGS

FIG. 6 is an exploded view showing the major components of another embodiment of the present invention;

DETAILED DESCRIPTION OF THE INVENTION INCLUDING ILLUSTRATIVE AND PREFERRED EMBODIMENTS

Figure 1:
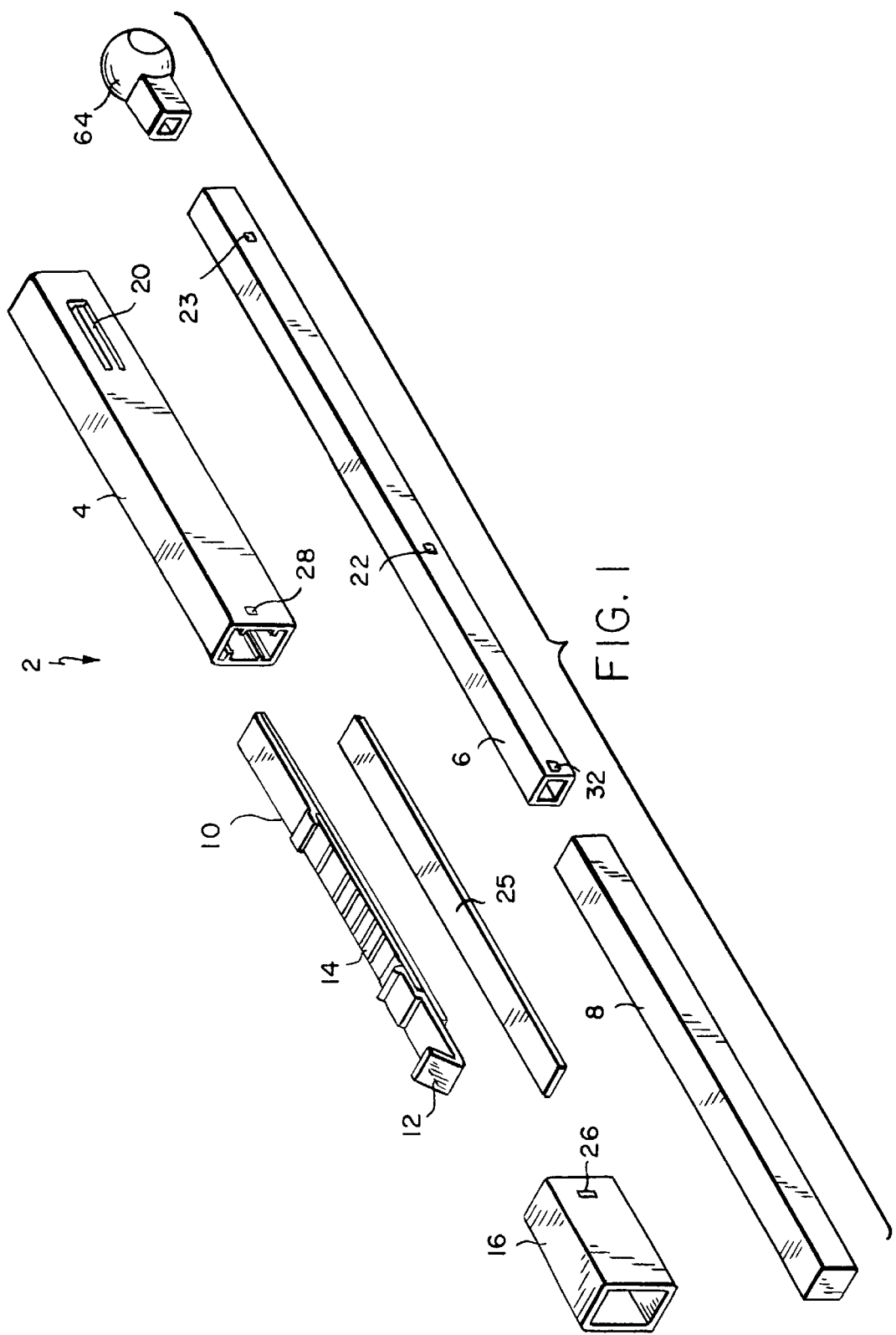
FIG. 1 is an exploded view showing the major components of one embodiment of the present invention.

The diagnostic testing device in accordance with the present invention will be described with reference to the drawings. FIG. 1 illustrates an embodiment of the present invention in an exploded view, wherein a diagnostic testing device 2 is made from a slide housing 4 that may be made from an extruded tube. In this illustrative embodiment, the slide housing 4 has a rectangular cross section.

Figure 2:
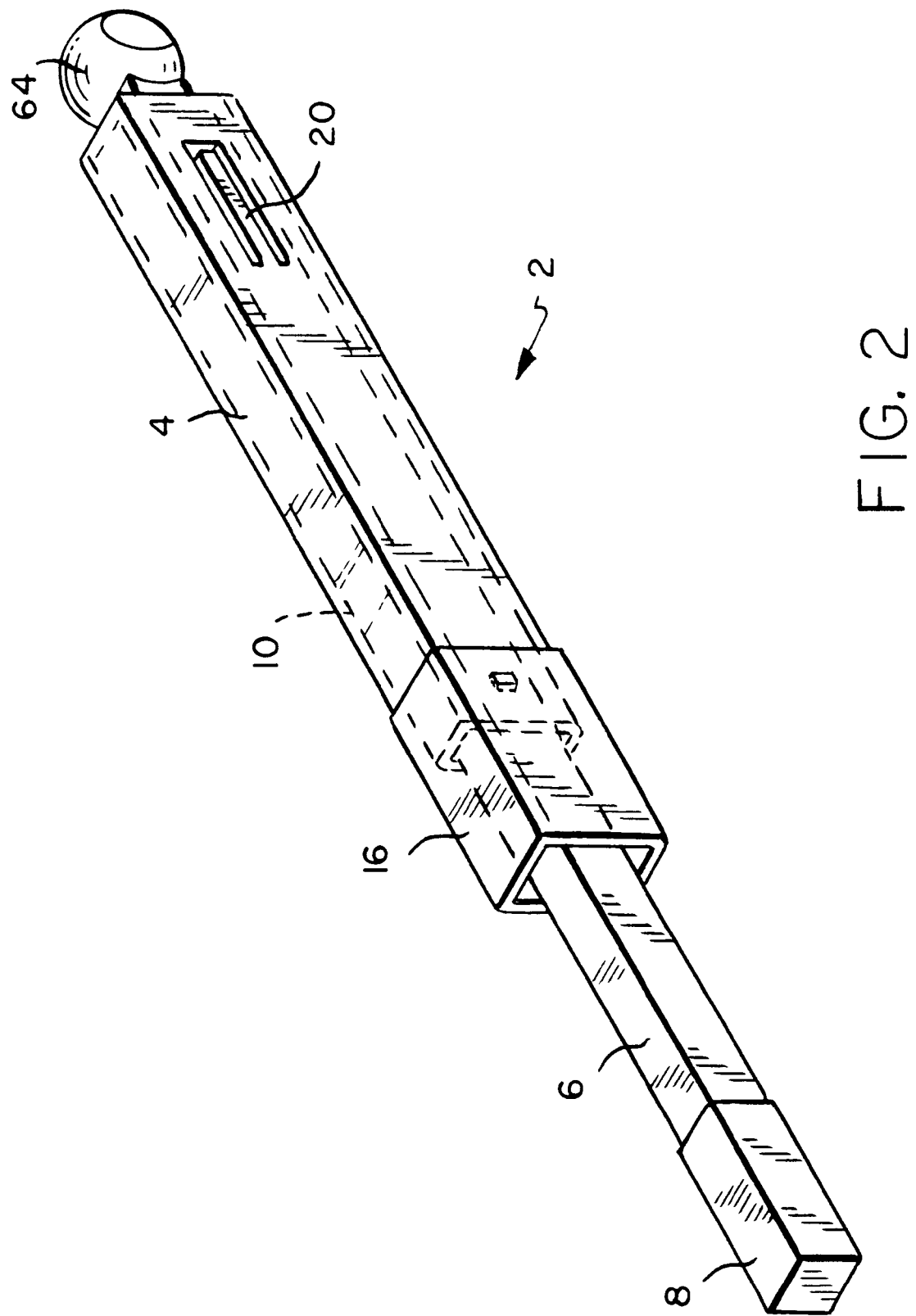
FIG. 2 is a simplified view of one illustrative embodiment of the diagnostic testing device of FIG. 1, illustrating the configuration of the device prior to delivery of a specimen to the test membrane in the housing.
Figure 3:
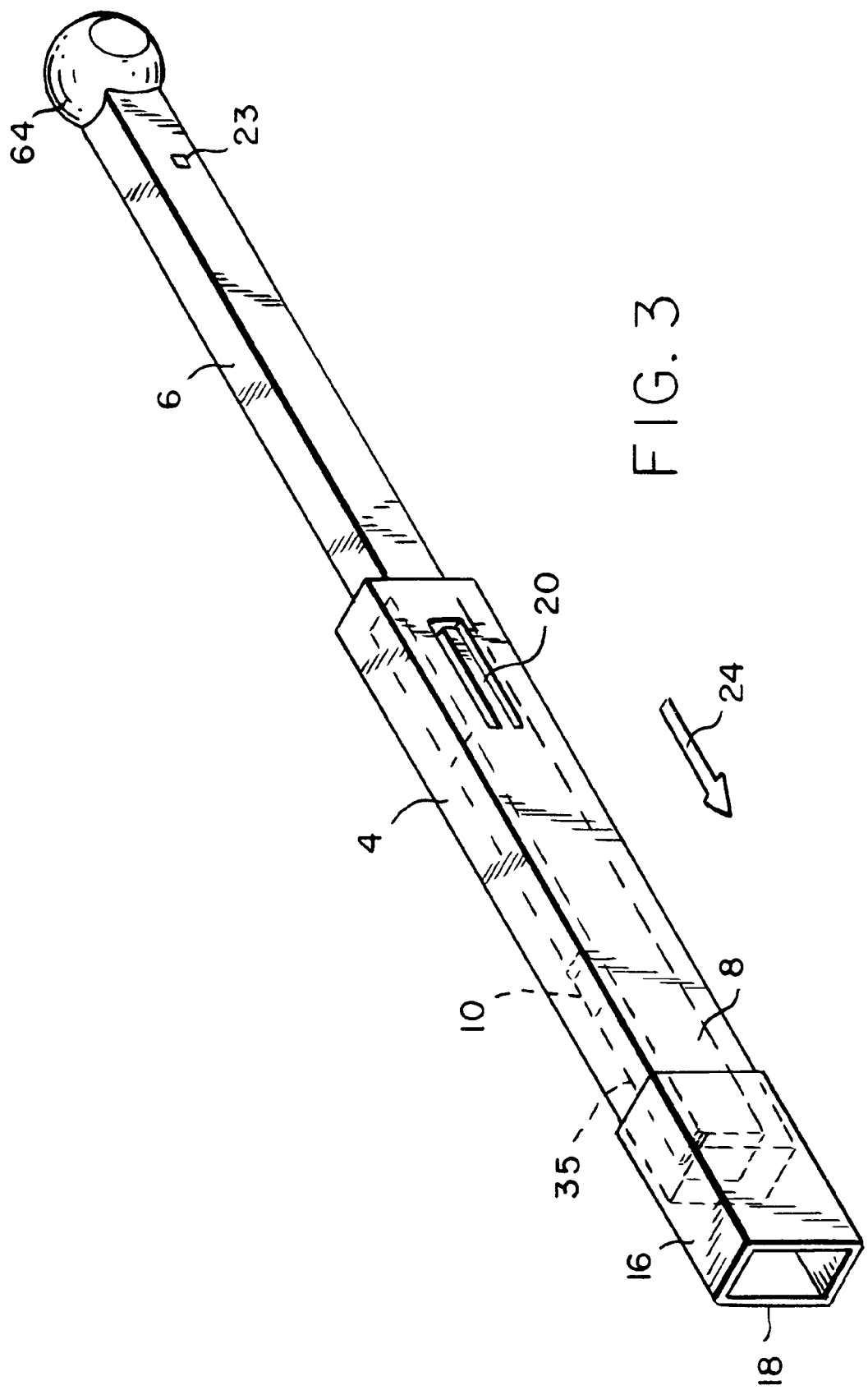
FIG. 3 is a simplified view of the diagnostic testing device of FIG. 1, illustrating the configuration of the device during delivery of a specimen to the test membrane in the housing.

In the illustrative embodiment of FIG. 1, a handle 6 is slidably received inside the slide housing 4 (see also FIGS. 2 and 3). The handle 6 can also be made of extruded tubing. The handle 6 is dimensioned so as to slide within the slide housing 4 without interference. A foam element 8 is disposed in the handle 6 so as to protrude from an end of the handle 6 a certain distance for collecting a fluid specimen (see also FIG. 2).

In the illustrative embodiment shown, the foam element 8 is compressible, and in its uncompressed state will have a cross section greater than the inside cross section of the handle 6 preferably to hold the foam in the elongated, hollow handle 6 without adhesive or other kinds of retainers. During assembly, the foam element 8 is compressed along its longitudinal axis and extruded or otherwise introduced into the handle 6, where it is circumscribed thereby.

Figure 4:
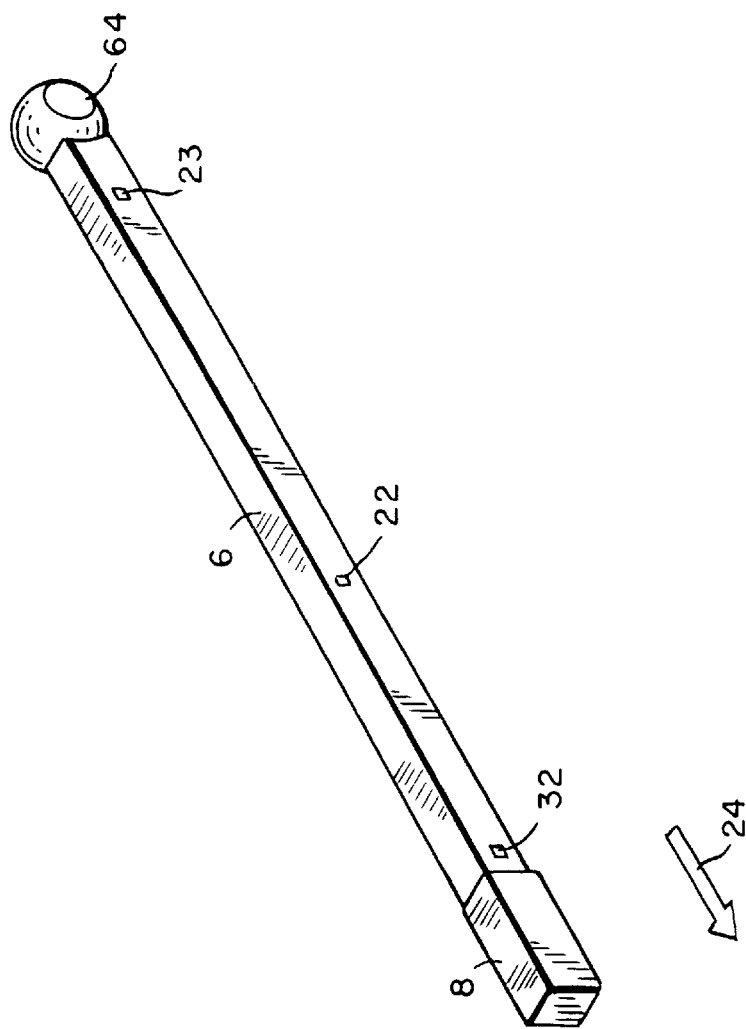
FIG. 4 is a simplified view of the diagnostic testing device of FIG. 1, illustrating the configuration of the device after removal of the housing.

At the end of the handle 6 opposite from the protruding portion of the foam element 8, the handle 6 receives an end cap 64, which provides a convenient gripping point for the user (see also FIGS. 2 through 4).

The protruding volume of the foam element 8 is the primary location for absorption of the sample for delivery to the test membrane and subsequent testing. The protruding volume of the foam element 8 is selected depending upon the type of fluid being sampled and the volume of fluid required for a particular diagnostic test. Generally, the foam element 8 will protrude from the end of the handle 6 a distance equal to about 25% to about 400% of the mean diameter of handle 6. If the handle 6 is not circular, the largest dimension of the cross section can be used to approximate the mean diameter for this purpose. Alternatively, the foam element 8 will generally protrude a distance of about 0.125 inch to about 2 inches from the end of the handle 6, depending upon the diameter of the handle 6. Preferably, the foam element 8 protrudes from the handle 6 a distance of one to three times the mean diameter of its uncompressed cross section for oral fluid collection, and about one to two times the mean diameter for urine collection.

In one preferred embodiment, the foam element 8 also extend into the hollow, elongated handle 6 for a sufficient distance to be retained in the handle 6. Generally, the foam element 8 should extend into the handle 6 a distance at least equal to the diameter of the handle's cross section. Preferably, the foam element 8 should extend into the handle 6 a distance at least equal to the length of the foam protruding from the handle 6. Of course, the foam can extend the full length of the handle 6 if desired.

The foam element 8 can be made of a variety of absorbent foams. Preferably, the foam is formed and cut to the desired size to expose the cell structure rather than a molded foam part having a surface skin. Preferred materials for the foam member include, e.g., polyurethane foam, polyethylene foam, polyvinylchloride foam, ethylvinylacetate foam, polyethylene/ethylvinylacetate foam, polyester foam and polyether foam. Absorbent Porex™, silicone and latex foams can also be used. Particularly useful foam for the collection of oral fluid is polyurethane foam sold under the mark HYDRASORB® by Avitar, Inc., Canton, Mass., USA. The preferred polyurethane foam has a uniform cell count of about 60 or more cells per linear inch. More preferably, the uniform cell count is about 80 to 120 cells per linear inch.

The handle 6 circumscribing the foam can be made of any suitable material having sufficient strength to compress and hold the foam member and to be handled during collecting and delivery of the specimen. Typical materials used for conventional straws, e.g., paper tubes and polyethylene, polypropylene, polyester, vinyl or other plastic tubes, are suitable for the handle 6. Straws also are economical and have an appropriate diameter for the manufacture, handling, and use of the diagnostic testing device. A rectangular cross section for the handle 6 is shown in FIGS. 1 through 4, but other shaped cross sections, such as circular, triangular, pentagonal, etc., could also be used.

Materials useful for the slide housing 4 can be the same materials useful for the handle 6. For example, paper tubes and polyethylene, polypropylene, polyester, vinyl or other plastic tubes are suitable for the slide housing 4. Any material can be used that has sufficient rigidity to maintain a shaped structure. The material should also be inert to a liquid sample for a sufficient time to complete testing. Those skilled in the art can readily select a suitable material from the wide variety of materials known for medical use and diagnostic testing. The slide housing 4 preferably should also be transparent if the diagnostic test is relatively instant and requires observing an optical property change on a test membrane.

As further seen in FIG. 1, the device 2 comprises a test membrane 10 that is retained in the slide housing 4 during delivery of the specimen (see also FIGS. 2 through 4). The test membrane 10 may be perforated or otherwise separated into discrete sections 14 and a reagent zone 29 (see FIG. 8), each carrying diagnostic test chemistry. The chemistry when in contact with specimen, as elaborated upon hereinbelow, forms the basis of a diagnostic test. Suitable diagnostic test chemistries are well known to those skilled in the art to diagnose a wide variety of substances such as, e.g., glucose, viruses, hormones, bacteria, alcohol, drugs of abuse, etc. Representative chemistries for the testing of glucose levels in whole blood are disclosed by Phillips in U.S. Pat. No. 4,935,346. Bronstein discloses in U.S. Pat. No. 4,978,614 chemistries for the detection of urinary components, and Zeng discloses test chemistries for detecting AIDS or other antibodies in EP 0 495 465. Generally, the preferred reagent will be a dry, immobilized chemistry, which is hydrated by incorporation of the liquid sample.

The test membrane 10 preferably comprises a strip, which is bent or curved to form a clip or folded retainer tab 12. The retainer tab 12, when the membrane is in situ, is further held in operative configuration by a membrane retaining/security hood 16. The retaining hood 16 can be held to the slide housing 4 by any conventional means, including a slot 26 and tab 28 arrangement as shown in FIG. 1, interference fits, and the like. Further, the retaining hood 16 can be equipped with a tamper-proof seal (not shown) to provide indicia that the device 2 has not been opened.

The device 2 preferably further comprises a confirmatory strip 25 that is also meant to be retained in the slide housing 4 during delivery of the specimen. The confirmatory strip 25 normally carries no diagnostic test chemistry and is therefore typically used to collect an amount of specimen. The confirmatory strip 25 can then be removed from the slide housing 4 for further tests such as gas chromatography or mass spectrometry testing.

FIG. 2 shows the device 2 primed for delivery of the specimen-containing foam element 8 to the test membrane 10 in the slide housing 4. The handle 6 typically is retained within the slide housing 4 during specimen collection. For example, the handle 6 is held in the slide housing 4 by any conventional means, including a locking tab detent 23 and locking tab 20 arrangement as shown in FIG. 1. Alternatively, the handle 6 is introduced into the slide housing 4 after the foam element 8 has been saturated with specimen. It is pointed out that in this illustrative embodiment, saturation of the foam element 8 will cause it to expand beyond its uncompressed dry cross-sectional dimension.

FIG. 3 depicts the delivery of the specimen to the test membrane 10. As the slide housing 4 is moved in the direction of arrow 24, the foam element 8 will pass into the slide housing 4 past the preferably rounded edge 18 of the retaining hood 16, and hence into contact with and past the test membrane 10. The handle 6 can be retained within the slide housing 4 during the delivery of the specimen to the test membrane 10. For example, the handle 6 can be held in the slide housing 4 by any conventional means, including a locking tab detent 22 (as shown in FIG. 1) and the locking tab 20 arrangement as shown in FIG. 1. In this arrangement, the handle 6 is held in the slide housing 4 so that the foam element 8 containing the fluid sample is in contact with a sample receiving zone 35 (see also FIG. 8) of the test membrane 10.

Because the cross sectional area of the inside of the slide housing 4 is smaller than that of the expanded wet foam element 8, the foam element 8 will be compressed, thereby causing the expression of specimen onto the sample receiving zone 35 of the test membrane 10 and allowing ample topical delivery to the test membrane 10. Capillary action will also serve to extract liquid from the foam element 8 to the test membrane 10. As stated above, a preferred embodiment of the invention utilizes a hydrophilic microporous material for the test membrane 10, whereby capillary action carries the liquid into the test membrane 10 so that the hydrostatic forces resulting from compression of the foam member 8 are not relied upon for the operability of the device.

For example, the exposed portion of the dry foam member 8 can have a reduced lateral cross sectional area (not shown), and be retained in the handle 6 by interference fit, or through the use of adhesives or other known means. In this embodiment, the protruding portion of the foam member 8 is sized to expand when wet so that it undergoes little or no compression as it makes contact with and moves past the test membrane 10 during delivery of the liquid sample to the test membrane 10. Alternatively, the protruding portion of the dry foam member 8 may have a cross sectional area (not shown) that is larger than that of the portion of the foam member 8 disposed in the handle 6 and, when wet, therefore larger than the cross sectional area of the inside of the slide housing 4. Again, the foam member 8 can be retained in the handle 6 by interference fit, or through the use of adhesives or other known means. Further, hydrostatic forces resulting from the compression of the protruding portion will assist in the delivery of the liquid sample to the test membrane 10.

Figure 8:
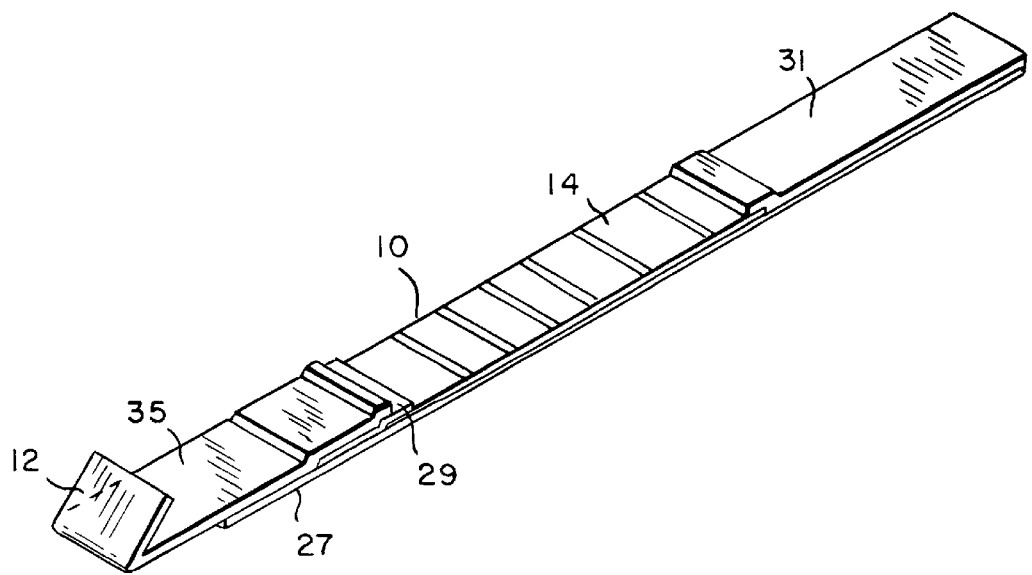
FIG. 8 is a simplified view of the test membrane system used with the diagnostic testing device of FIG. 1.

Preferably, the micropore size of the test membrane 10 will be in the range of 0.05 to 30 $\mu$, and more preferably in the range of 0.1 to 20 $\mu$. A liquid sink zone 31 (see also FIG. 8) is provided on the test membrane 10 for absorbing excess liquid that might be conducted by capillary action through the length of the test membrane 10. As shown in FIG. 8, the test membrane 10 also includes a membrane support 27 for integrally supporting the sample receiving zone 35, the reagent zone 29, the membrane zone 14, and the liquid sink zone 31.

FIG. 4 shows the handle 6 removed from the slide housing 4 after delivery of specimen to the test membrane 10. At this point, the handle 6 is discarded. The locking tab 20 on the slide housing 4 preferably forms a ratcheting mechanism with a locking tab detent 32 on the handle 6, thereby preventing the handle 6 from being reinserted into the slide housing 4 after the specimen has been applied to the test membrane 10. In some instant tests, such as drug testing, bacteriological testing, the testing of urinary ketones or simple pH testing, the results of the diagnostic test may be read directly on the test membrane 10 through a transparent slide housing 4 without the need of disassembling the device 2. In some tests, such as DNA tests or for confirmatory testing purposes, the slide housing 4 can be mailed in a sealed container to a laboratory for additional processing and obtaining results. In some tests, such as some viral tests, the retaining hood 16 can be removed in the theatre of use and the test membrane 10 removed for additional processing, such as the application of additional reagents.

Figures 5A, 5B:
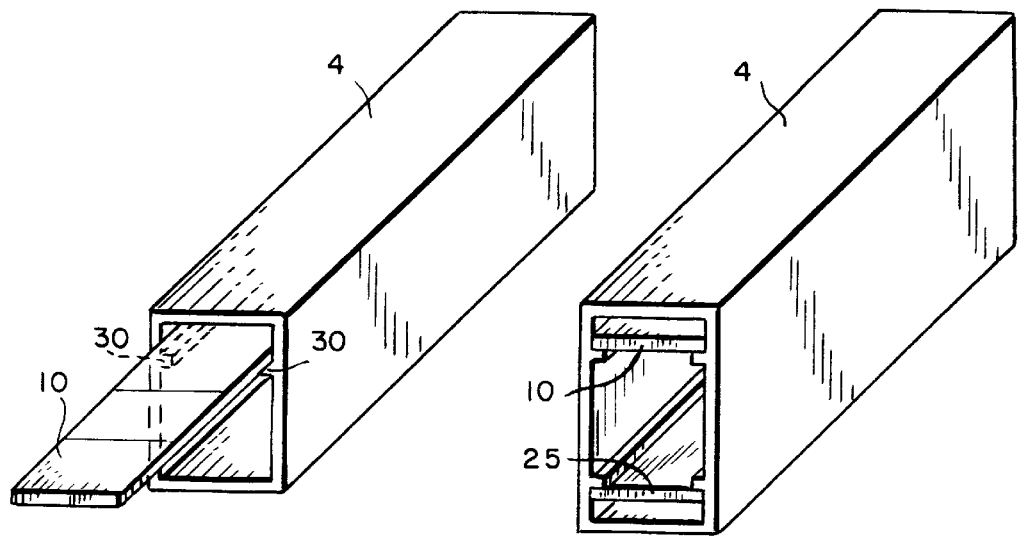
FIGS. 5a through 5f are isometric views of slide housings used with alternative embodiments of the present invention.

The illustrative embodiment having a square cross section of slide housing 4 is shown in FIG. 5a. Here, retaining members or ribs 30 are disposed to allow the sliding placement of either one test membrane 10 or one confirmatory strip 25 into the slide housing 4. The choice of how many test membranes 10 or confirmatory strips 25 are to be placed in the slide housing 4 will dictate the number of ribs 30, as seen in FIG. 5b, in which the slide housing 4 accommodates, e.g., one test membrane 10 and one confirmatory strip 25. The handle 6 used in this or any embodiment must only slidably fit within the internal bore of the slide housing 4, and need not share the exact geometry thereof. For example, the handle 6 may have a circular cross section, or two or more handles 6 may be provided which together fit within the bore of the slide housing 4.

Figures 5C, 5D:
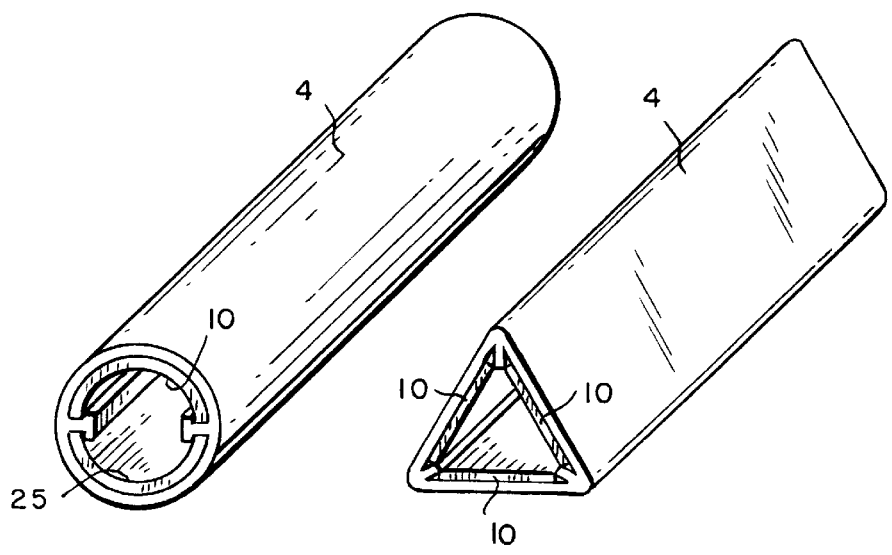

FIG. 5c shows another illustrative embodiment of the present invention, where the housing 4 comprises a circular cross section. This configuration can be desirable from a cost of manufacture point of view because stock tubing can be used, which is typically inexpensive. In this embodiment, one test membrane 10 and one confirmatory strip 25 can be accommodated, which are held as depicted in compression so as to bow into substantially semi-circular configurations and into contact with the interior wall of the housing 4. Alternatively, this embodiment can accommodate two test membranes 10 or two confirmatory strips 25.

FIG. 5d shows still another illustrative embodiment of the present invention, where the slide housing 4 comprises a triangular cross section. In this embodiment, up to three test membranes 10 or confirmatory strips 25, or any useful combination thereof, can be accommodated.

Figure 5E:
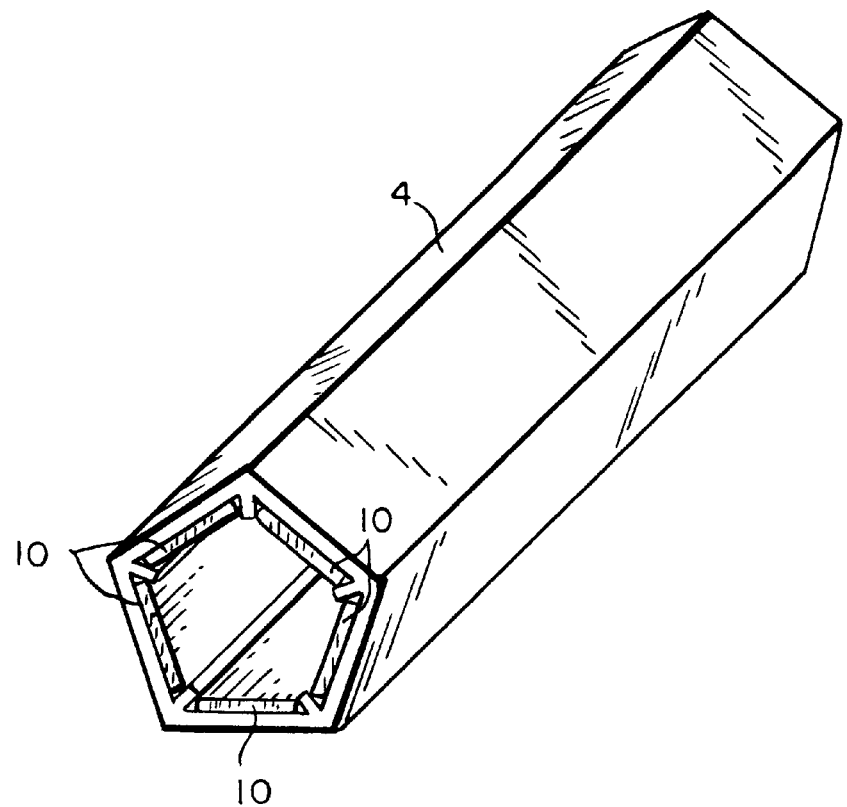

FIG. 5e shows yet another illustrative embodiment of the present invention, where the slide housing 4 comprises a pentagonal cross section. In this embodiment, up to five test membranes 10 or confirmatory strips 25, or any useful combination thereof, can be accommodated.

Figure 5F:
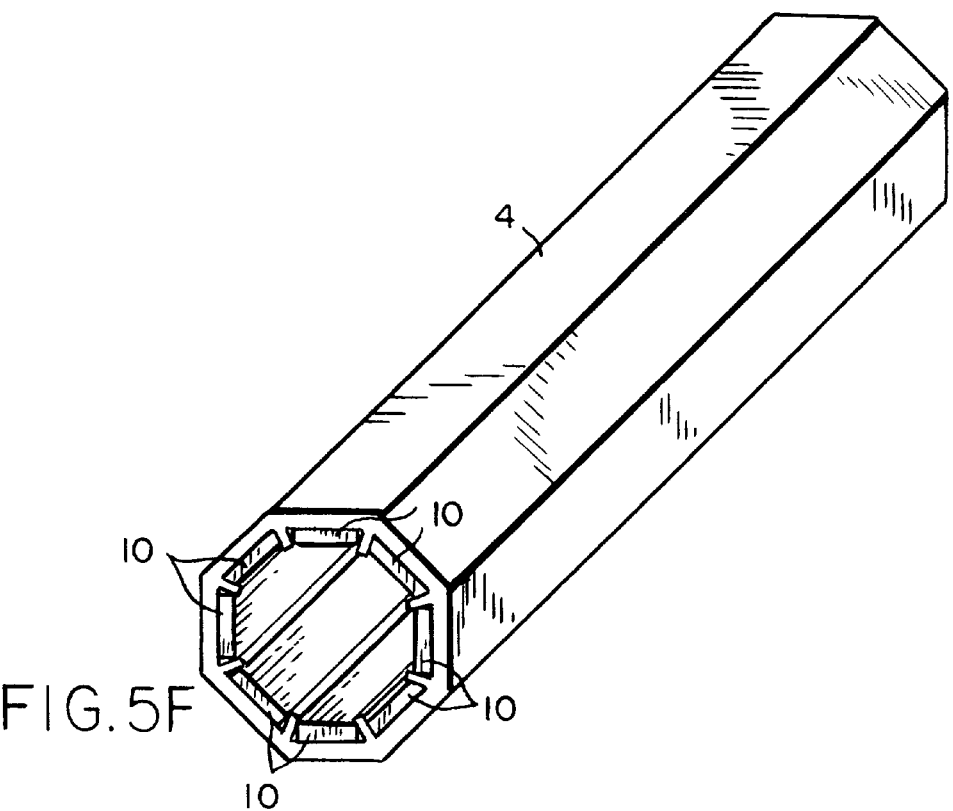

FIG. 5f shows yet still another illustrative embodiment of the present invention, where the slide housing 4 comprises an octagonal cross section. In this embodiment, up to eight test membranes 10 or confirmatory strips 25, or any useful combination thereof, can be accommodated.

FIG. 6 shows another illustrative embodiment of the present invention in an exploded view. The device 40 comprises a housing 42 that receives in mating fashion a handle 44. The handle 44 has a cross section that is received in the bore 48 of the housing 42 in a snugly fitting relationship (see also FIG. 7). A foam member 50 is likewise inserted into the bore 48 from the end of the housing 42 opposite to the handle 44 (see also FIG. 7). When handle 44 and foam member 50 are both inserted into bore 48 of housing 42, end face 46a of the handle 44 is in contact with the end of foam member 50. The handle 44 supports a diagnostic test membrane 52, which has a portion 45 extending along the end face 46a of handle 44. Sections 56 of the test membrane 52 contain the test chemistries, which are positioned on the lateral face 46b of the handle 44 (see also FIG. 7). At the end of the handle 44 opposite to the forward face 46a, the handle 44 has an internal bore (not shown) with a depth sufficient for receiving an end cap 49, which provides a convenient gripping point for the user. Alternatively, the handle 44 and the end cap 49 may be provided as one piece. The housing 42 and the end cap 49 may be advantageously provided with texture gripping surfaces (not shown) to aid in separation. Preferably, housing 44 has at least one side, along which the test membrane 52 is positioned, that is made of a clear material. Alternatively, the side of the housing, along which the test membrane 52 is positioned, has a window to permit observation of the test membrane.

Figure 7:
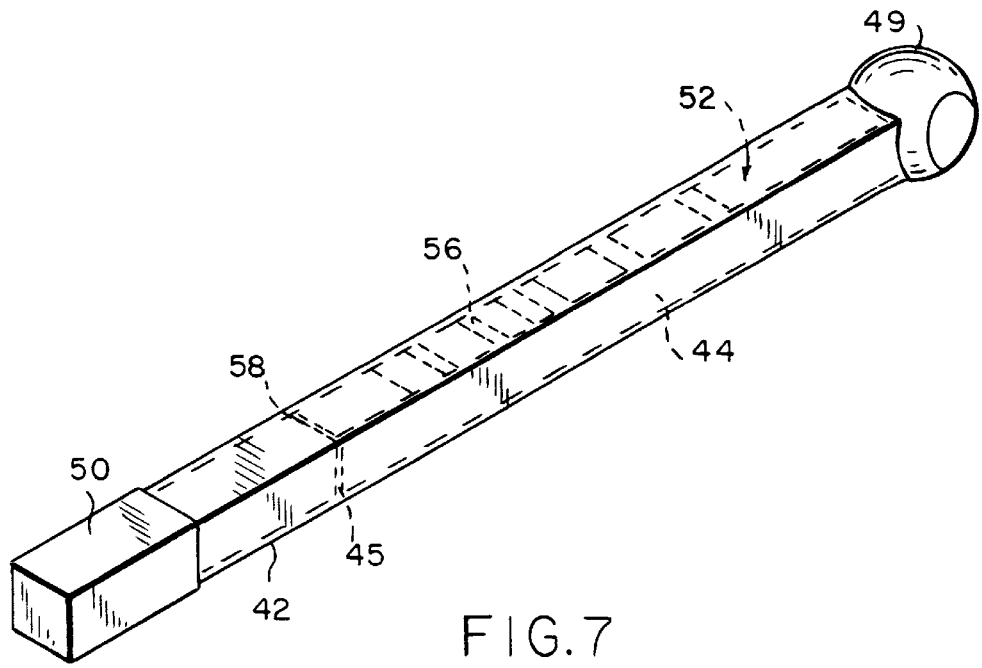
FIG. 7 is a simplified view of the diagnostic testing device of FIG. 6, illustrating the configuration of the device during delivery of a specimen to the test membrane in the housing.

FIG. 7 depicts the delivery of the specimen to the test membrane 52. When the handle 44 with the diagnostic test membrane 52 supported thereon is inserted into the bore 48, the test membrane 52 resides substantially entirely within the bore 48. The foam member 50 is inserted into the bore 48 as described above such that its edge 58 is contacting a face portion 45 (see also FIG. 6) of the test membrane 52. With this embodiment, capillary action or other fluid transport mechanisms of the test membrane delivers the sample to the test chemistries. The housing 42 can be advantageously molded from transparent plastic to aid in viewing the test chemistries. The housing 42 with the foam member 50 can be discarded after the membrane is read.

To collect a sample using any of the above described embodiments, a liquid sample, e.g., oral fluid or urine, or the like, can be collected by wicking the fluid into the foam member in as little as 15 seconds by touching the foam member to a liquid specimen. The foam member is sized in accord with the test being performed and the type of specimen collected for the test.

The diagnostic testing device of the present invention is particularly useful to provide liquid samples extracted from the foam for diagnostic analysis or identification of drugs, antibodies, DNA, RNA, and the like.

The diagnostic testing device of the present invention also is useful for collecting samples of oral fluid and spotting the samples from the foam onto a membrane for subsequent isolation of DNA for PCR. After delivery of the specimen to the membrane (called "spotting"), the sample is dried. DNA is isolated from the spotted sample for analysis using a PCR technique (see, e.g., Cheng et al., *Proc. Natl. Acad. Sci. USA*. 91:5695–5699 or Wright et al., *J. Clin. Microbiol.* 32: 464–468). The collection matrix can be a conventional paper matrix or, preferably, a collection matrix sold under the brand name IsoCode™ by Schleicher & Schuell, Keene, N.H. 03431.

A particularly useful diagnostic membrane for the practice of the present invention is described in copending application Ser. No. 09/123,376 filed Jul. 27, 1998, the disclosure of which is hereby incorporated by reference. It describes a diagnostic test membrane comprising a porous membrane having a sample receiving zone containing a fatty sarcosinate surfactant, reagent chemistry including antibodies to a particular analyte that are freely mobile when the membrane is moist, and spaced from the sample receiving zone a detection zone for detecting the presence of said particular analyte, the detection zone containing immobilized molecules of said particular analyte that are not free to move when the membrane is moist. A detectable change is produced in the detection zone when antibodies bind to the immobilized analyte. Preferably the detectable change is a visible change, such as production of a color. Also preferably, a control zone is provided downstream of the detection zone, wherein the presence of the sample causes a detectable change, preferably a visible change. The detection of change in the control zone can denote the presence of sufficient sample in the diagnostic test membrane. A liquid sink zone can also be provided further downstream from the control zone, e.g., at an opposite end of the diagnostic test membrane from the sample receiving zone. Of course, the zones can also be constructed in annular rings around the sample receiving zone.

The porous membrane is preferably positioned for contact with the foam member after collection of the fluid sample.

A microporous nitrocellulose layer is coated with stripes of suitable chemicals to provide the test zone and control zone. A layer of solution containing the appropriate chemicals is coated in the surface of the nitrocellulose in a stripe to form each zone. By controlling the amount of solution laid down, the width of the zones can be controlled with a suitable distance between the zones being devoid of chemicals. The coated layer is then dried, cut into the desired size. Any suitable membrane material can be used, for example, a 0.5μ nitrocellulose microporous filter membrane.

A reagent zone is made by imbibing reagent chemicals into a fibrous polyvinyl or polyester filter layer to provide the appropriate concentration and drying the layer. Any suitable filter material can be used, for example, a 1.2μ hydrophilized polypropylene filter material (SA3J853F0) sold by Millipore Corporation (Bedford, Mass.). After drying the reagents, the membrane is cut into the desired size and positioned on the nitrocellulose membrane.

The sample receiving zone is made by imbibing a solution containing a suitable buffer and a fatty acid sarcosinate into a sheet of non-woven material to provide the appropriate concentration. The buffer is selected for the analyte and specimen for which the test strip is designed. A preferred fatty acid sarcosinate is sodium myristoyl sarcosinate, which is provided at a concentration of about 1.0 wt %. The fatty acid sarcosinate surfactant can be obtained from Hampshire Chemical Corporation, which manufactures and sells such surfactants under the brand name Hamposyl. The surfactant sold as Hamposyl M30 is sodium myristoyl sarcosinate. Preferably, the fatty acid sarcosinate is present in the imbibing solution at a concentration of from about 0.1% to about 10% by weight. The sheet is dried, cut into the desired size and positioned adjacent the reagent zone. The non-woven material can be, for example, any conventional filter material such as 470 paper (Cat. No. 539929) or 740 paper (Cat. No. 539930), which are available from Schleicher and Schuell.

The bibulous matrix can be any of a variety of materials having a porous structure for absorption of aqueous fluids, for example, non-woven fibrous materials including paper and microporous polymer membranes including foam membranes.

Another preferred bibulous material is a polyurethane foam membrane. Preferably, heat and pressure are applied to at least one surface of the polyurethane foam to enhance its use as a diagnostic membrane. The treated surface can absorb fluid more readily, maintain a greater attraction for the fluid as compared to the untreated foam membrane, and provide for a linear flow of fluid at the surface through capillary action. Suitable reagents can be applied to zones on the surface of the treated foam membrane for detecting a particular analyte in a diagnostic test.

Before treatment, the open cell polyurethane foam material preferably has an average cell size of approximately 0.005 inch to about 0.02 inch in diameter. The thickness of the foam material is preferably about 0.1 to about 0.125 inch. This material is treated with temperature and pressure to permanently partially collapse the cell structure such that the surface of the foam is provided with small cells or pores and/or reticulated formations. The characteristics of the surface will vary depending upon the particular temperature and pressure used. These characteristics can range from cells that are not completely collapsed or fused and, in general, have an average cell size, for example, of about 0.005 inch in diameter to a treated surface wherein the cells are virtually eliminated leaving a reticulated structure. The altered structure continues for a measurable depth into the base foam material. The depth can range preferably from about 0.001 inch to about one-half of the thickness of the base material, more preferably from about 0.01 to about 0.02 inch. The greater density in the treated area has been found to promote capillary flow through the modified structure. The treated area appears to retain fluid and only when it has become overly saturated does it expel fluid into the less absorbent macrocellular area of the foam membrane. Thus, the macrocellular layer becomes a reservoir for excess fluid.

The cells are collapsed preferably by heating the polyurethane foam to a temperature near its softening point, which can range from about 300 F. to about 450 F. depending upon the pressure used. Pressures ranging from about 5 psi to about 120 psi can be used, more preferably 60 psi. The particular temperature and pressure to obtain the desired result can be found by routine experimentation. Both sides of the base material can be treated utilizing heated rollers or platens; however, treating one side is sufficient for use as a diagnostic membrane. Silicon coated release paper or coatings on the rollers or platens can be used for ease of processing.

The invention has been described in detail with reference to preferred embodiments thereof. However, it will be appreciated that, upon consideration of the present specification and drawings, those skilled in the art may make modifications and improvements within the spirit and scope of this invention as defined by the claims.

What is claimed is:

1. A specimen collecting and testing device comprising:

a housing having a bore and retaining members in the bore for receiving at least one membrane, the membrane carrying diagnostic test chemistry;

at least one hollow handle member being dimensioned to be slidably received in the bore of the housing; and an elongated foam member having a length along a longitudinal axis and being circumscribed by the handle member along a portion of the length, the foam member having a portion protruding from an end of the handle member for collecting specimen, the protruding portion being dimensioned to be slidably received in the bore of the housing for making contact with the membrane after collecting the specimen, whereby the foam member is protruding from the housing for sample collection and the protruding portion of the foam member is drawn across the membrane as the handle member is drawn through the bore of the housing, thereby delivering the collected specimen to the membrane.

2. The specimen collecting and testing device of claim 1, wherein the housing is made of paper or plastic.

3. The specimen collecting and testing device of claim 1, wherein the foam member comprises a material selected from the group consisting of polyurethane foam, polyethylene foam, polyvinylchloride foam, ethylvinylacetate foam, polyethylene/ethylvinylacetate foam, polyester foam and polyether foam.

4. The specimen collecting and testing device of claim 1, wherein the hollow handle member is made of paper or plastic.

5. The specimen collecting and testing device of claim 1, wherein the foam member comprises a polyurethane foam.

6. The specimen collecting and testing device of claim 1, wherein the foam member protrudes from an end of the handle member a distance of about 25% to about 400% of mean diameter of an uncompressed cross sectional area of the foam member.

7. The specimen collecting and testing device of claim 1, further comprising a retaining member dimensioned to sidably receive an end of the housing, the retaining member for mechanically preventing the membrane from sliding from the bore of the housing.

8. The specimen collecting and testing device of claim 7, wherein the retaining member further comprises one of a tab or a slot, and wherein the housing contains one of a mating tab or slot for receiving the tab or the slot on the retaining member for maintaining said retaining member on the housing.

9. The specimen collecting and testing device of claim 2, wherein the housing comprises a transparent plastic.

10. The specimen collecting and testing device of claim 1, wherein the handle member comprises a plurality of handle members that may all be slidably received in the bore of the housing at the same time.

11. The specimen collecting and testing device of claim 1, wherein the membrane further comprises a retaining clip for holding the membrane in the bore of the housing.

12. A method of collecting a sample of fluid specimen for diagnostic testing, the method comprising:
    providing a specimen collecting and testing device including
        a housing having a bore and retaining members in the bore for receiving at least one membrane, the membrane carrying diagnostic test chemistry,
        at least one hollow handle member being dimensioned to be slidably received in the bore of the housing, and
        an elongated foam member having a length along a longitudinal axis and being circumscribed by the handle member along a portion of the length, the foam member having a portion protruding from an end of the handle member and housing for collecting specimen, the protruding portion being dimensioned to be slidably received in the bore of the housing for making contact with the membrane after collecting the specimen;
    wetting the protruding portion of the foam member with specimen; and
    sliding the hollow handle member through the bore of the housing, thereby drawing the protruding portion of the wetted foam member across the membrane and delivering the collected specimen to the membrane.

13. The method of claim 12,
    wherein the step of providing at least one hollow handle member comprises providing a plurality of handle members, and
    wherein the step of sliding the handle member through the bore of the housing comprises sliding all of the handle members through the bore at the same time.

14. The method of claim 12,
    further comprising the step of removing the membrane from the housing after the delivery of the specimen for further processing.

15. A specimen collecting and testing device comprising:
    a housing member having a first end and a second end and a bore therethrough connecting said first and second ends;
    at least one membrane carrying diagnostic test chemistry and including a face portion for receiving specimen; and
    an elongated foam member having a length along a longitudinal axis and an end portion for collecting specimen,
    wherein the housing member circumscribes a portion of the elongated foam member and is adapted to receive and hold the face portion of the membrane in contact with the elongated foam member, thereby enabling delivery of the specimen to the membrane within the housing member whereby the foam member protrudes form the housing for sample collection.

16. The specimen collecting and testing device of claim 15,
    further comprising
    a membrane holder having a portion with a forward face adapted to be received in mating fashion inside the bore at the first end of the housing, the portion adapted to be received in the bore further carrying the membrane with the face portion of the membrane disposed on the forward face,
    wherein the circumscribed portion of the foam member is received in mating fashion inside the bore from the second end of the housing, and
    wherein the circumscribed portion of the foam member at least partially contacts the face portion of the membrane when the membrane holder is inserted into the bore at the first end of the housing.

17. The specimen collecting and testing device according to claim 15,
    wherein the housing is made of paper or plastic.

18. The specimen collecting and testing device according to claim 15,
    wherein the foam member comprises a material selected from the group consisting of polyurethane foam, polyethylene foam, polyvinylchloride foam, ethylvinylacetate foam, polyethylene/ethylvinylacetate foam, polyester foam and polyether foam.

19. The specimen collecting and testing device of claim 16,
    wherein the membrane holder member is made of paper or plastic.

20. The specimen collecting and testing device of claim 15,
    wherein the foam member comprises a polyurethane foam.

21. The specimen collecting and testing device of claim 15,
    wherein the foam member protrudes from the second end of the housing a distance of about 25% to about 400% of mean diameter of an uncompressed cross sectional area of the foam member.

22. The specimen collecting and testing device of claim 17,
    wherein the housing comprises a transparent plastic.

23. A method for collecting a sample of fluid specimen for diagnostic testing, the method comprising the steps of:
    providing a specimen collecting and testing device comprising
        a housing member having a first end and a second end and a bore therethrough connecting said first and second ends,
        at least one membrane carrying diagnostic test chemistry and including a face portion for receiving specimen, and
        an elongated foam member having a length along a longitudinal axis and an end portion which protrudes from the housing for collecting the specimen,
        wherein the housing member circumscribes a portion of the elongated foam member and is adapted to receive and hold the face portion of the membrane in contact with the elongated foam member, thereby enabling delivery of the specimen to the membrane within the housing member;
    wetting the end portion of the foam member with specimen; and
    delivering the specimen to the membrane by capillary action.

24. The method of claim 23,
    wherein the step of providing a specimen collecting and testing device further comprises
    providing a membrane holder having a portion with a forward face adapted to be received in mating fashion inside the bore at the first end of the housing, the portion adapted to be received in the bore further carrying the membrane with the face portion of the membrane disposed on the forward face,
    wherein the circumscribed portion of the foam member is adapted to be received in mating fashion inside the bore from the second end of the housing, and
    wherein the circumscribed portion of the foam member at least partially contacts the face portion of the membrane when the membrane holder is inserted into the bore at the first end of the housing.

25. A specimen collecting and testing device comprising:

a handle member having a first end and a second end and a bore therethrough;

at least one membrane carrying diagnostic test chemistry;
an elongated foam member having a length along a longitudinal axis and an uncompressed cross sectional area in a plane perpendicular to the longitudinal axis,
wherein the handle member is adapted to removably receive a first portion of the elongated foam member at the first end thereof and the foam member has a second portion protruding from the first end for collecting specimen; and a housing member adapted to receive the membrane and comprising a bore slidably receiving the handle member, wherein the handle member is adapted to be adjusted to protrude form the housing for collecting the specimen and adapted to be withdrawn from the housing member for contacting the protruding second portion of the foam member to the membrane, thereby delivering the specimen to the membrane.

26. The specimen collecting and testing device of claim 25, wherein the handle member further comprises a handle cap at the second end.

27. The specimen collecting and testing device of claim 25, wherein the handle member and the housing member are made of paper or plastic.

28. The specimen collecting and testing device according to claim 25, wherein the foam member comprises a material selected from the group consisting of polyurethane foam, polyethylene foam, polyvinylchloride foam, ethylvinylacetate foam, polyethylene/ethylvinylacetate foam, polyester foam and polyether foam.

29. The specimen collecting and testing device of claim 25, further comprising a security hood attached to the housing member.

30. The specimen collecting and testing device of claim 25, wherein the foam member comprises a polyurethane foam.

31. The specimen collecting and testing device of claim 25, wherein the foam member protrudes from the first end of the handle member a distance of about 25% to about 400% of mean diameter of the uncompressed cross sectional area of the foam member.

32. The specimen collecting and testing device of claim 25, wherein the housing member comprises a transparent plastic.

33. A method for collecting a sample of fluid specimen for diagnostic testing, the method comprising:

providing a specimen collecting and testing device comprising
a handle member having a first end and a second end and a bore therethrough,
at least one membrane carrying diagnostic test chemistry,
an elongated foam member having a length along a longitudinal axis and an uncompressed cross sectional area in a plane perpendicular to the longitudinal axis,
wherein the handle member is adapted to removably receive a first portion of the elongated foam member at the first end thereof and the foam member has a second portion protruding from the first end for collecting specimen, and
a housing member adapted to receive the membrane and comprising a bore slidably receiving the handle member, wherein the handle member is adapted to be adjusted to protrude form the housing for collecting the specimen and adapted to be withdrawn from the housing member for contacting the protruding second portion of the foam member to the membrane, thereby delivering specimen to the membrane;

wetting the protruding second portion of the foam member with specimen; and delivering the specimen to the membrane by capillary action.

34. A specimen collecting and testing device comprising:

at least one membrane carrying diagnostic test chemistry;

an elongated foam member having a length along a longitudinal axis and an uncompressed cross sectional area in a plane perpendicular to the longitudinal axis; and a housing member circumscribing a portion of the elongated foam member which is adapted to protrude from the housing, and the housing member is adapted to receive and hold said membrane for contact with the elongated foam member, whereby a fluid sample collected by the foam member is transferred to said membrane for diagnostic testing.

* * * * *